United States Patent [19]

Burgess et al.

[11] Patent Number: 5,648,502

[45] Date of Patent: Jul. 15, 1997

[54] REGIOSELECTIVE SYNTHESIS OF 4-CHLORO-2-THIOPHENECARBOXYLIC ACID

[75] Inventors: Laurence E. Burgess, Gales Ferry; Gary R. Schulte, Stonington, both of Conn.

[73] Assignee: Pfizer Inc., New York, N.Y.

[21] Appl. No.: 436,415

[22] PCT Filed: Sep. 17, 1993

[86] PCT No.: PCT/US93/08613

§ 371 Date: Jul. 7, 1995

§ 102(e) Date: Jul. 7, 1995

[87] PCT Pub. No.: WO94/12505

PCT Pub. Date: Jun. 9, 1994

Related U.S. Application Data

[63] Continuation of Ser. No. 979,983, Nov. 23, 1992, abandoned.

[51] Int. Cl.$^6$ ..................................................... C07F 7/02
[52] U.S. Cl. ........................ 549/4; 548/406; 548/468; 549/71
[58] Field of Search ..................... 549/4, 71; 548/406, 548/468

[56] References Cited

U.S. PATENT DOCUMENTS

| 4,432,974 | 2/1984 | Haber | 424/184 |
| 5,047,554 | 9/1991 | Ehrgott et al. | 548/486 |
| 5,118,703 | 6/1992 | Reiter et al. | 514/414 |
| 5,498,630 | 3/1996 | Phillion et al. | 514/443 |

FOREIGN PATENT DOCUMENTS

| 0216279 | 4/1987 | European Pat. Off. . |
| 0393936 | 10/1990 | European Pat. Off. . |
| 2655655 | 6/1991 | European Pat. Off. . |

OTHER PUBLICATIONS

M. Lemaire et al., J. Electroanal. Chem., vol. 281, 292–298 (1990).

J. Iriarte et al., J. Heterocyclic Chem., vol. 13, 393–394 (1976).

T. Greene, "Protective Groups in Organic Synthesis", pp. 39–43, John Wiley & Sons, New York (1981).

*Primary Examiner*—Richard L. Raymond
*Attorney, Agent, or Firm*—Peter C. Richardson; Gregg C. Benson; James T. Jones

[57] ABSTRACT

4-Chloro-2-thiophenecarboxylic acid is made by forming a compound of formula (Ia), disclosed herein, wherein $R^3$ is ($C_1$–$C_6$) alkyl, phenyl, or benzyl; converting the compound to a compound of formula (IVa), disclosed herein, and removing the silyl group $R_3Si$—. The product is useful as an intermediate in making pharmaceutical products.

10 Claims, No Drawings

REGIOSELECTIVE SYNTHESIS OF 4-CHLORO-2-THIOPHENECARBOXYLIC ACID

This is a §317 application of PCT/US93/08613, filed Sep. 17, 1993, which in turn continues from U.S. application Ser. No. 07/979,983, filed Nov. 23, 1992, now abandoned.

4-Chloro-2-thiophenecarboxylic acid has the structure

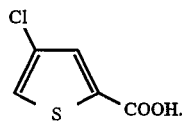

(VI)

It is an important intermediate for the synthesis of pharmaceutical compounds such as, for example, 5-fluoro-6-chloro-3-(4-chloro-2-thenoyl)-2-oxindole-1-carboxamide which is disclosed in Example 72 of U.S. Pat. No. 5,047,554 to Ehrgott et al.

A synthesis of 4-chloro-2-thiophenecarboxylic acid (herein also abbreviated for convenience as "CTCA") is disclosed by J. Iriarte et al., J. Heterocyclic Chem., 13, 393 (1976). It is there reported that CTCA was obtained in quantitative yield in crude form by oxidizing the corresponding 2-aldehyde with silver oxide. The crude acid was reported to have a melting point (m.p.) of 124°–126°. The product was further stated to have a melting point of 131°–132° following "repeated crystallization from methanol or dichloromethane." Iriarte et al. also report, in the same paper, making CTCA, m.p. 125°–126°, by saponifying ethyl 4-chlorothiophene-2-carboxylate in methanolic potassium hydroxide, the carboxylate having been made by the direct chlorination of ethyl thiophene-2-carboxylate in the presence of aluminum chloride.

Lemaire et al., J. Electroanal. Chem., 281, 293, (1990) report, inter alia, making 3-chloro-2-trimethylsilylthiophene by a method employing a Grignard reagent, the product being used in an electropolymerization to make poly(3-chlorothiophene). Neither CTCA nor any method for synthesizing it is disclosed.

The present inventors have now determined that CTCA can be produced by a temperature-dependent regioselective process in which potentially reactive sites are blocked and thus prevented from contributing by-products.

SUMMARY OF THE INVENTION

In its broadest aspect, this invention provides a process of making 4-chloro-2-thiophenecarboxylic acid, comprising removing the silyl group $SiR_3$ from a compound of formula IVa

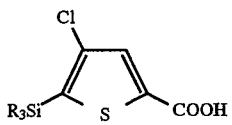

(IVa)

wherein each of the R groups is independently selected from $(C_1-C_6)$alkyl, benzyl, and phenyl.

A variation of the above process for making 4-chloro-2-thiophenecarboxylic acid, comprises removing the silyl group $SiR_2$ from a compound of formula IVb

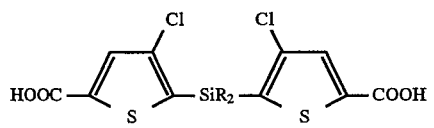

(IVb)

wherein R is as previously defined.

In greater detail, a process of making 4-chloro-2-thiophenecarboxylic acid, comprises the steps of:

1) treating 3-chlorothiophene, at a temperature less than about −50° C., with base, followed by treatment with a silyl compound of the formula $R_3SiX$, wherein X is a leaving group and each of the R groups is independently selected from $(C_1-C_6)$alkyl, benzyl, and phenyl, thereby forming a compound of the formula

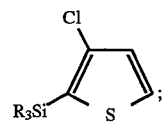

(Ia)

2) treating the product of step (1), at a temperature less than about −50° C., with a base sufficient to deprotonate at the 5-position of the chlorothiophene ring, thereby correspondingly forming an anion of formula IIa

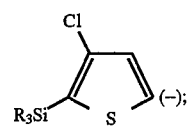

(IIa)

3) treating the product of step (2), at a temperature less than −50° C., with carbon dioxide to form, correspondingly, the monocarboxylate of formula IIIa

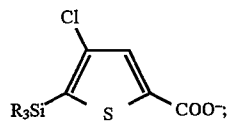

(IIIa)

4) converting the product of step (3) to the corresponding acid (i.e. of formula IVa); and 5) removing the silyl group $SiR_3$.

A variation of the immediately preceding process for making 4-chloro-2-thiophenecarboxylic acid comprises the steps of:

1) treating 3-chlorothiophene, at a temperature less than about −50° C., with base, followed by treatment with a silyl compound of the formula $R_2SiX_2$, wherein X and R are as previously defined, thereby forming a compound of the formula

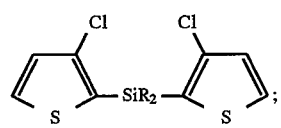

(Ib)

2) treating the product of step (1), at a temperature less than about −50° C., with a base sufficient to deprotonate at the 5 and 5' positions of the two thiophene rings, thereby correspondingly forming a dianion of formula IIb

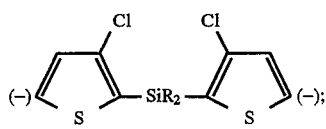

(IIb)

3) treating the product of step (2), at a temperature less than −50° C., with carbon dioxide to form the corresponding dicarboxylate of formula IIIb

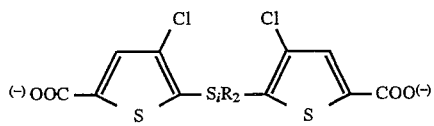
(IIIb)

4) converting the product of formula step (3) to the corresponding diacid (i.e. of formula IVb); and 5) removing the silyl group $SiR_2$.

As leaving groups "X", halogeno groups including chloro, bromo, and iodo, trifluoromethanesulfonate, trifluoroacetate, acetamide, trifluoroacetamide, 1,2,4-triazole, and imidazole are useful, along with others known to the art. Chloro and trifluoromethanesulfonate are preferred due to their wide commercial availability.

Particular values of R as $(C_1-C_6)$alkyl include methyl, ethyl, n-propyl, isopropyl, n-butyl, isobutyl, tert-butyl, and n-hexyl.

CTCA produced by the above process is believed to be substantially pure and exhibits a melting point of 138° C., indicating a much greater purity than that of prior art products which exhibit a melting point of only 131°–132° even after repeated recrystallization.

This invention further provides processes (which are variations) of making 5-fluoro-6-chloro-3-(4-chloro-2-thenoyl)-2-oxindole-1-carboxamide (structure VIII, Scheme I infra), comprising reacting, in the presence of a base, 5-fluoro-6-chloro-2-oxindole-1-carboxamide (structure VII, Scheme I) with an activated form (for example the acid chloride, acylimidazole, or methyl ester) of 4-chloro-2-thiophenecarboxylic acid produced according to any of the above-described processes. It is preferred to use either the activated acylimidazole produced by reacting CTCA with carbonyldiimidazole or the acid chloride produced by reacting CTCA with thionyl chloride. Both of these preferred activated derivatives can be formed in a conventional manner.

A further process of making 5-fluoro-6-chloro-3-(4-chloro-2-thenoyl)-2-oxindole-1-carboxamide comprises the steps of:

(1) reacting, in the presence of a base, 5-fluoro-6-chloro-2-oxindole-1-carboxamide with an activated monocarboxylic acid having the formula IVc:

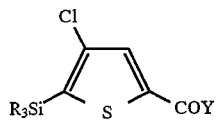
(IVc)

wherein Y is chloro, imidazol-1-yl, or methyl, thereby correspondingly forming a 5-fluoro-6-chloro-3-(4-chloro-3-trisubstitutedsilyl-2-thenoyl)-2-oxindole-1-carboxamide of formula Va;

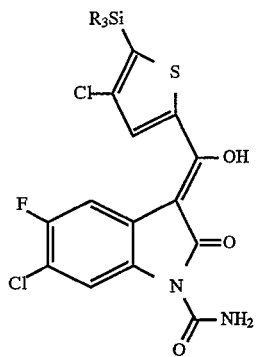
(Va)

and (2) removing the silyl group $SiR_3$.

A variation of the process described immediately above comprises the steps of:

(1) reacting, in the presence of a base, 5-fluoro-6-chloro-2-oxindole-1-carboxamide with an activated dicarboxylic acid having the formula IVd

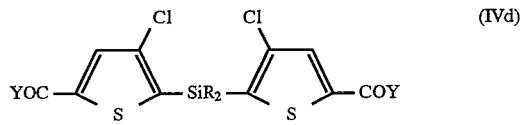
(IVd)

wherein Y is as previously defined, thereby correspondingly forming a compound of formula Vb;

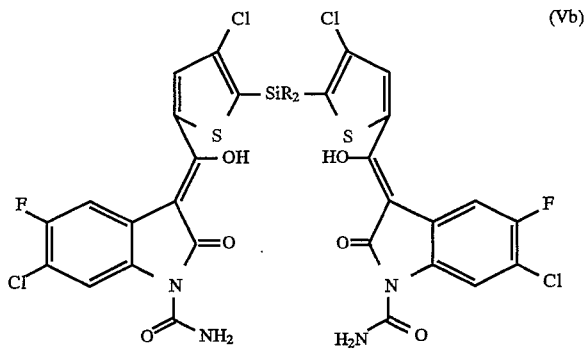
(Vb)

and (2) removing the silyl group $SiR_2$.

Compounds having formulae IVa and IVb are also believed to be novel and are accordingly provided as an additional feature of the invention.

The chemistry of this invention, using silanes of formula $R_3SiX$ for exemplification, can be summarized in generalized flowchart form as follows:

Scheme I

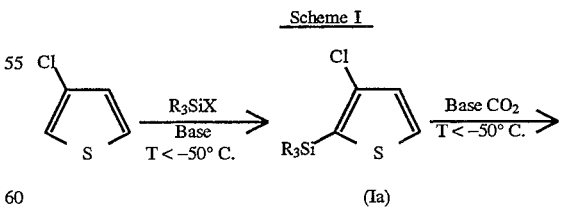
(Ia)

-continued
Scheme I

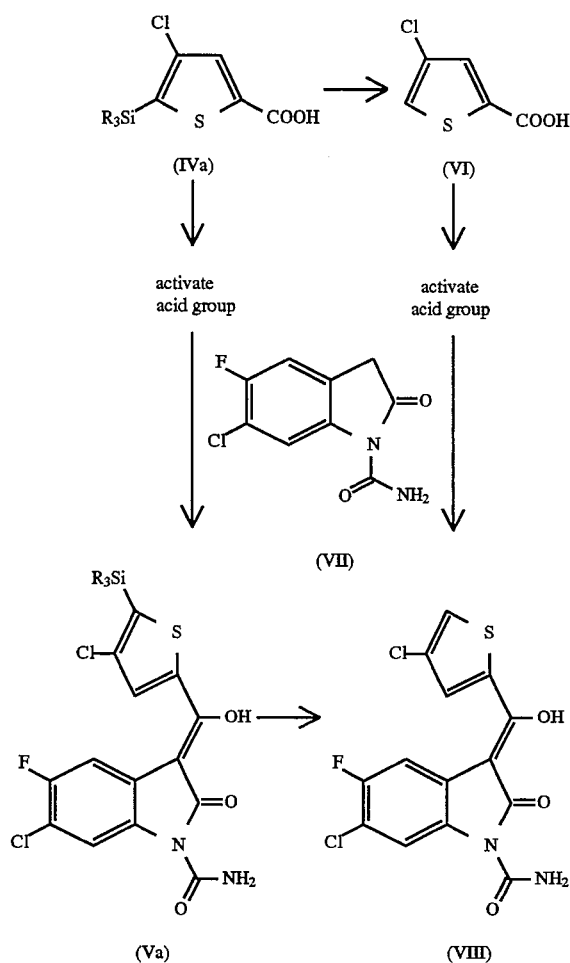

Those skilled in the art will appreciate that the use of a silyl compound of formula R₂SiX₂, in lieu of a silyl compound of formula R₃SiX, results, correspondingly, in replacing, in Scheme I, the mono-derivative of formula Ia with the dimerized 3-chlorothiophene of formula Ib, supra, in replacing the mono-acid of formula IVa with the bis-acid of formula IVb, and in replacing the mono-derivative of formula Va with the bis-derivative of formula Vb, supra.

DETAILED DESCRIPTION OF THE INVENTION

As a preliminary matter, it is noted that all of the reactions described following should be run under an inert atmosphere, with either argon or nitrogen being preferred. For the sake of convenience the silyl blocking groups R₃Si— (and —R₂Si—) are referred to in the following description simply as "blocking groups", and the silyl compounds R₃SiX (and R₂SiX₂) are referred to as "blocking reagents". It is further noted that when a temperature less than about −50° C., and preferably less than −70° C., is specified, a −78° C. temperature is preferred due to the ease of implementing it with a dry ice/acetone bath. Lower temperatures are feasible, for example, a temperature of −94° C. which can be implemented by cooling a hexane bath with liquid nitrogen. However, no significant advantage is thereby obtained.

3-Chlorothiophene blocked at the 2-position can be made by first treating 3-chlorothiophene with an equivalent amount of a strong base, such as an alkyllithium, at a temperature below −50° C., preferably below −70° C., so that deprotonation is regioselective and favors the 2-position. n-Butyllithium is preferred as the base due to its ready commercial availability. The 3-chlorothiophene and base are dissolved in inert solvents ("inert" being used with reference to the reaction conditions employed) such as tetrahydrofuran (THF) and hexane, respectively. The reaction mixture is stirred for a period of time which can range from one-half an hour to several hours. At this point the blocking reagent can be added in equivalence, or in slight (up to 10%) excess. After a period of time ranging from a few minutes to hours, the reaction mixture can then be quenched after warming to about room temperature or less by adding water and/or brine. The blocked product can then be extracted into an appropriate organic solvent such as ethyl acetate in a conventional manner, dried, and isolated conventionally as by evaporation.

The 2-blocked-3-chlorothiophene can then be reacted, in an appropriate dry solvent such as THF, with a base (equivalence or slight excess) at a temperature less than −50° C., preferably less than −70° C., to selectively deprotonate at the remaining unblocked carbon atom adjacent to the thiophene sulfur atom. While maintaining the temperature below −50° C., carbon dioxide gas can then be used to treat the deprotonated intermediate and thereby effect carbon dioxide capture to yield the 4-chloro-5-blocked-2-thiophene carboxylate of formula IIIa or IIIb. Those skilled in the art will appreciate the desirability of employing a base which does not provide better nucleophilic properties than the blocking reagent and which, accordingly, will not attack and displace the blocking group already attached to the thiophene ring. Useful bases for this step include lithiumdialkylamides which can conveniently be generated in situ by reacting an alkyllithium compound with a dialkylamine. For example, n-butyllithium can be treated at about 0° C. in THF, prior to the introduction of the 2-blocked-3-chlorothiophene formed in the previous step, with an equivalent amount of a dialkylamine such as diisopropylamine, thereby forming lithium diisopropylamide. The temperature can then suitably be lowered to below −50° C. and carbon dioxide capture effected. The carboxylate is converted to the acid by quenching the reaction with aqueous acid, for example, aqueous hydrochloric acid. The organic layer can then be separated, the aqueous portion extracted (for example, using ethyl acetate), and the acid isolated.

At this point the blocking group can be removed by treating the product with fluoride to yield 4-chloro-2-thiophene carboxylic acid. The acid may then be activated and reacted with 5-fluoro-6-chloro-2-oxindole-1-carboxamide (also referred to herein as the "carboxamide precursor") to yield the medicinal product 5-fluoro-6-chloro-3-(4-chloro-2-thenoyl)-2-oxindole-1-carboxamide.

Alternatively, the blocking group need not be removed and the blocked acid can be activated and reacted directly with the carboxamide precursor to yield the correspondingly blocked medicinal product (Va) or (Vb).

In either case, as stated, the blocking group can be removed by treatment with fluoride anion, with the final medicinal product being isolated on quenching the reaction with aqueous (e.g. hydrochloric) acid. The source of fluoride ion is not critical, and a relatively wide range of fluoride-containing reagents can be employed, including alkali metal fluorides (for example sodium, potassium, lithium, and cesium fluoride), alkaline earth metal fluorides (for example magnesium and calcium fluoride), hydrogen fluoride in both free (HF) and bound (for example as pyridinium hydrofluoride) forms, and tetra-loweralkylammonium fluorides. Tetra-loweralkylammonium fluorides are preferred, with tetra-n-butylammonium fluoride being particularly preferred because of its ready commercial availability. An excess of fluoride, say 2–3 equivalents, can be employed to facilitate the reaction.

Methods for using 5-fluoro-6-chloro-3-(4-chloro-2-thenoyl)-2-oxindole-1-carboxamide are taught in Ehrgott, U.S. Pat. No. 5,047,554.

The following Examples illustrate various aspects of the invention but are not to be construed as limiting in any way the scope thereof. In the Examples, NMR data was obtained from Brooker AM 250 and Brooker AM 300 instruments. Frequencies employed for $^1H$ (proton) NMR spectra were 250 MHz or 300 MHz. $^{13}C$ NMR spectra were obtained at 62.5 MHz or 75 MHz.

EXAMPLE 1a

2-Trimethylsilyl-3-chlorothiophene

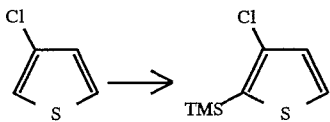

To 3-chlorothiophene (5.0 g, 42.16 mmol), dissolved in 50 mL of tetrahydrofuran stirring at −72° C. (acetone/dry ice bath), was added 16.8 ml of 2.5M hexane solution of n-butyllithium over a 15 minute period. The reaction temperature was maintained below −70° C. during the addition. Soon after complete addition of the n-butyllithium a white precipitate formed. After 40 minutes of stirring below −70° C., 5.88 mL of chlorotrimethylsilane was slowly added over a 5 minute period. After addition the solution momentarily became clear before turning cloudy again by the formation of lithium chloride by-product. After 10 minutes the reaction solution was warmed to 0° C. At 0° C. 5 mL of water followed by 25 mL of brine was added to quench the reaction. The aqueous solution was then extracted with ethyl acetate (2×30 mL). The organic extract was dried ($Na_2SO_4$), filtered and evaporated to 8.0 g of title compound as a clear oil.

Physical properties: Mass Spectrum (EIMS) m/z=192($M^+$+2, 14%), 190($M^+$, 36%), 177($M^+$+2—$CH_3$, 41%), and 175($M^+$—$CH_3$, 100%); $^1HNMR(CDCl_3)\delta 7.49(1H, d, J=4.7 Hz)$, 7.07(1H, d, J=4.7 Hz), and 0.46(9H, s); $^{13}CNMR(CDCl_3)$ $\delta 132.0$, 130.2, 130.1, 129.8, and −0.7.

EXAMPLE 1b

4-Chloro-5-trimethylsilyl-2-thiopene Carboxylic Acid

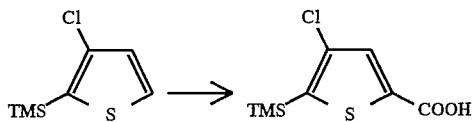

A small (4 mg) sample of diphenylacetic acid was dissolved in 50 mL of tetrahydrofuran and stirred at room temperature. To this solution was slowly added dropwise n-butyllithium as a 2.5M hexane solution until the solution turned light yellow from the diphenylacetic acid dianion. This protocol ensures that the solution is dry. At this point the solution was cooled to −72° C. (acetone/dry ice). Once at this temperature 4.62 mL (11.542 mmol) of a 2.5M hexane solution of n-butyllithium was added followed by 1.76 mL (12.592 mmol) of diisopropylamine. For formation of lithium diisopropyl amide the reaction solution was raised to 0° C. (ice bath) for 20 minutes and then lowered again to −72° C. To the cold reaction solution was added 2.0 g (10.493 mmol) of 2-trimethylsilyl-3-chlorothiophene as a 5 mL tetrahydrofuran solution over a 20 minute period. Reaction pot temperature was maintained below −70° C. to ensure regioselective deprotonation. After 30 minute reaction time carbon dioxide gas was slowly bubbled through the yellow solution. During the bubbling the reaction temperature was kept below −55° C. Total carbon dioxide treatment lasted 10 minutes. Following carbon dioxide addition the solution was gradually warmed to 0° C. at which point the reaction was quenched with 50 mL of 1N hydrochloric acid causing some gas evolution. On addition of the acidic solution the reaction was brought to room temperature. A 50 mL volume of brine was also added. The organic layer was separated and the aqueous was extracted with ethyl acetate (2×50 mL). The organic extracts were combined, washed with brine (1×50 mL), dried (sodium sulfate), filtered, and evaporated to 2.38 g of a white solid. Recrystallization of the crude product with heptane gave 1.67 g of pure title compound as small white needles, mp=206°–210° C.

Physical Properties: Mass Spectrum (LSIMS) m/z=237 ($M+H^+$+2, 12%) and 235($M+H^+$,10%); $^1HNMR(CDCl_3)$ $\delta 7.74(1H, s)$ and 0.41(9H, s); $^{13}CNMR(CDCl_3+CD_3OD)$ $\delta 163.1$, 141.2, 137.8, 134.7, 131.6 and −1.4.

EXAMPLE 1c

4-Chloro-2-thiophene Carboxylic Acid

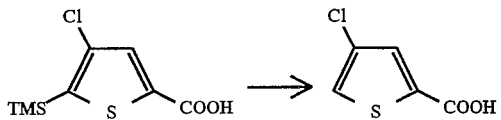

A 300 mg (1.278 mmol) sample of 4-chloro-3-trimethylsilyl-2-thiophene carboxylic acid was dissolved in 10 mL of tetrahydrofuran with 0.3 mL of water and cooled to −5° C. (ice/brine bath). A 2.6 mL aliquot of the 1M tetrahydrofuran solution of tetra-n-butyl ammonium fluoride was slowly added to the reaction solution. After 4 hours the reaction was poured into 50 mL of 5% aqueous sodium bicarbonate. The entire reaction solution was transferred to a separatory funnel and washed with ethyl acetate (2×25 mL). The basic aqueous solution was acidified with concentrated hydrochloric acid to pH2 and then extracted with ethyl acetate (3×30 mL). The organic extract was then dried (sodium sulfate), filtered, and evaporated to 216 mg of product as a white solid. Recrystallization using hot heptane gave 85 mg of pure crystalline product, mp 138° C.

Physical Properties: Mass Spectrum (EIMS) m/z 164($M^+$+2, 30%) and 162($M^+$, 100%); $^1HNMR(CDCl_3)\delta 10.9(1H, br s, exchangeable)$, 7.74(1H, d, J=1.5Hz), and 7.43(1H, d, J=1.5 Hz); $^{13}CNMR(CDCl_3)\delta 166.1$, 134.6, 133.2, 128.3, and 126.5.

EXAMPLE 2a

5-Fluoro-6-chloro-2,3-dihydro-3-[hydroxy-2-(4-chloro-5-trimethylsilylthienyl)methylene]-2-oxo-1H-indole-1-carboxamide

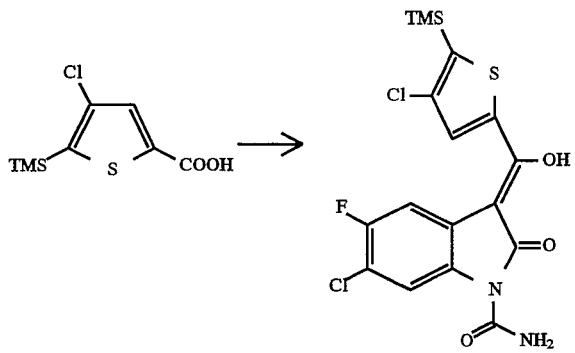

A 375 mg (1.60 mmol) sample of 4-chloro-5-trimethylsilyl-2-thiophene carboxylic acid was combined with 5 mL of thionyl chloride and heated to reflux. After 1.5 hours the reaction was complete. The flask was slowly cooled to room temperature and the excess thionyl chloride was evaporated to give the expected acid chloride as a brown oil. This brown oil was dissolved in 5 mL of N,N-dimethylformamide and slowly added to a 15 mL N,N-dimethylformamide solution of 5-fluoro-6-chloro-2,3-dihydro-2-oxo-1H-indole-1-carboxamide(500 mg, 2.24 mmol) and 4-(N,N-dimethylamino)pyridine(708 mg, 5.80 mmol) stirring at 0° C. After 1 hour the reaction was poured into 30 mL of 1N hydrochloric acid causing the product to precipitate as a maroon solid. The crude solid was filtered and recrystallized from hot acetic acid to give 307 mg (0.69 mmol) of pure title compound as a yellow crystalline solid, mp=200° C.

Physical Properties: Mass Spectrum (LSIMS)m/z 470 (M—H $^+$+Na$^+$+4, 4%), 468 (M—H$^+$+Na$^+$+2, 16%), 466 (M—H$^+$+Na$^+$, 21%), 448(M$^+$+4, 17%), 446(M$^+$+2, 74%), 444(M$^+$, 100%), 405(M$^+$—CONH+4, 8%), 403(M$^+$—CONH+2, 28%) and 401 (M$^+$—CONH, 39%); $^1$HNMR (DMSO-d$_6$)δ8.97(1H, exchangeable), 8.51(1H, s), 8.11 (1H, d, J$_{H-F}$=7.3 Hz), 7.96(1H, d, J$_{H-F}$=11.0 Hz), 7.30(1H, exchangeable), 6.21(1H, exchangeable), and 0.37(9H, s).

EXAMPLE 2b

5-Fluoro-6-chloro-2,3-dihydro-3-[hydroxy-2-(4-chloro-thienyl)methylene]-2-oxo-1H-indole-1-carboxamide

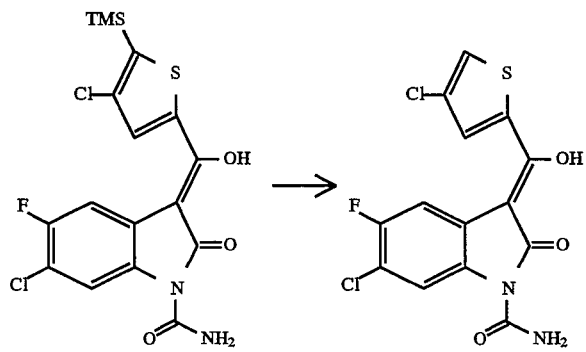

A 50 mg (0.11 mmol) sample of 5-fluoro-6-chloro-2,3-dihydro-3-[hydroxy-2-(4-chloro-5-trimethyisilylthienyl)methylene]-2-oxo-1H-indole-1-carboxamide was dissolved in 2 mL of tetrahydrofuran and cooled to 5° C. A small 0.56 mL aliquot of a 1M tetrahydrofuran solution of tetra-n-butylammonium fluoride was added by syringe to the stirring cold solution of the indole substrate. After 1 hour 0.25 mL of water was added to the reaction. After an additional 30 minutes the reaction was quenched by the addition of 5 mL of 1N hydrochloric acid. The reaction contents were then poured into 15 mL of water. This caused precipitation of the product. Filtration gave 25 mg of desired title product, as a yellow solid which was recrystallized from acetic acid to give a crystalline product, mp=234°–237° C.

Physical Properties: $^1$HNMR(DMSO-d$_6$)δ9.10(1H, exchangeable), 8.69 (1H, d, J=1.5 Hz), 8.10 (1H, d, J$_{H-F}$=7.4 Hz), 8.06(1H, d, J$_{H-F}$=11.4 Hz), 7.65(1H, d, J=1.5 Hz), and 7.26(1H, exchangeable).

We claim:

1. A compound having the formula IVa

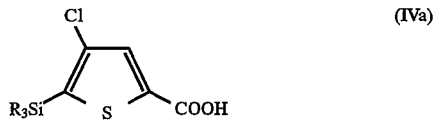 (IVa)

or IVb

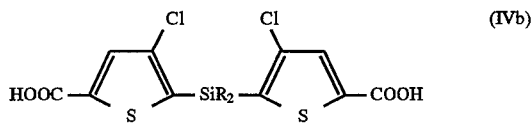 (IVb)

wherein each R group is independently selected from (C$_1$–C$_6$)alkyl, benzyl, and phenyl.

2. A process of making 4-chloro-2-thiophenecarboxylic acid, comprising removing the silyl group SiR$_3$ from a compound of formula IVa

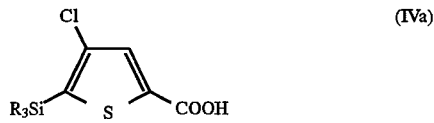 (IVa)

wherein each R group is independently selected from (C$_1$–C$_6$)alkyl, benzyl, and phenyl.

3. A process of making 4-chloro-2-thiophenecarboxylic acid, comprising removing the silyl group SiR$_2$ from a compound of formula IVb

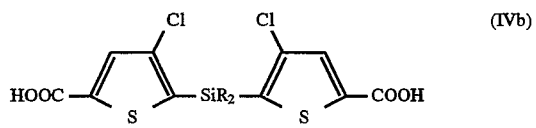 (IVb)

wherein each R group is independently selected from (C$_1$–C$_6$)alkyl, benzyl, and phenyl.

4. A process of making 4-chloro-2-thiophenecarboxylic acid, comprising the steps of:

1) treating 3-chlorothiophene, at a temperature less than about –50° C., with base, followed by treatment with a silyl compound of the formula R$_3$SiX, wherein X is a leaving group and each of the R groups is independently selected from (C$_1$–C$_6$)alkyl, benzyl, and phenyl, thereby forming a compound of the formula

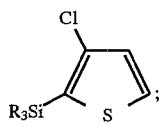 (Ia)

2) treating the product of step (1), at a temperature less than about −50° C., with a base sufficient to deprotonate at the 5-position of the chlorothiophene ring, thereby correspondingly forming an anion of formula IIa

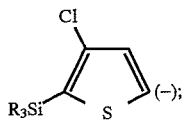 (IIa)

3) treating the product of step (2), at a temperature less than −50° C., with carbon dioxide to form, correspondingly, the monocarboxylate

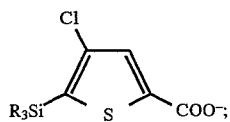 (IIIa)

4) converting the product of formula IIIa to the corresponding acid; and
5) removing the silyl group SiR₃.

5. A process as defined in claim 4, wherein R is methyl and X is chloro or trifluoromethanesulfonate, and wherein, in each of steps (1)–(3), said temperature is less than −70 C.

6. A process of making 4-chloro-2-thiophenecarboxylic acid, comprising the steps of:

1) treating 3-chlorothiophene, at a temperature less than about −50 ° C., with base, followed by treatment with a silyl compound of the formula R₂SiX₂, wherein X is a leaving group and each of the R groups is independently selected from (C₁–C₆)alkyl, benzyl, and phenyl, thereby forming a compound of the formula

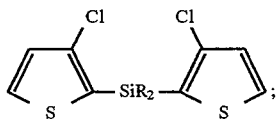 (Ib)

2) treating the product of step (1), at a temperature less than about −50° C., with a base sufficient to deprotonate at the 5 and 5' positions of the two thiophene rings, thereby correspondingly forming a dianion of formula IIb

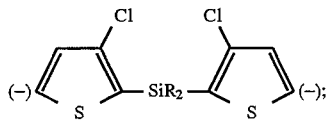 (IIb)

3) treating the product of step (2), at a temperature less than −50° C., with carbon dioxide to form, correspondingly the dicarboxylate

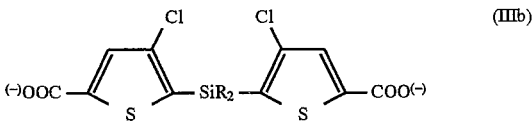 (IIIb)

4) converting the product of formula IIIb to the corresponding diacid; and
5) removing the silyl group SiR₂.

7. A process as defined in claim 6, wherein R is methyl and X is chloro or trifluoromethanesulfonate, and wherein, in each of steps (1)–(3), said temperature is less than −70° C.

8. A process of making 5-fluoro-6-chloro-3-(4-chloro-2-thenoyl)-2-oxindole-1-carboxamide, comprising reacting, in the presence of a base, 5-fluoro-6-chloro-2-oxindole-1-carboxamide with 4-chloro-2-thiophene carboxylic acid produced by the process of claim 4 or claim 5.

9. A process of making 5-fluoro-6-chloro-3-(4-chloro-2-thenoyl)-2-oxindole-1-carboxamide, comprising the steps of:

(1) reacting, in the presence of a base, 5-fluoro-6-chloro-2-oxindole-1-carboxamide with a monocarboxylic acid having the formula

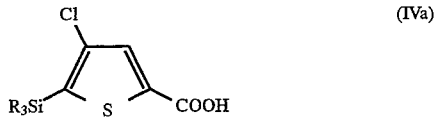 (IVa)

thereby correspondingly forming a 5-fluoro-6-chloro-3-(4-chloro-3-trisubstitutedsilyl-2-thenoyl)-2-oxindole-1-carboxamide; and (2) removing the silyl group SiR₃.

10. A process of making 5-fluoro-6-chloro-3-(4-chloro-2-thenoyl)-2-oxindole-1-carboxamide, comprising the steps of:

(1) reacting, in the presence of a base, 5-fluoro-6-chloro-2-oxindole-1-carboxamide with a dicarboxylic acid having the formula

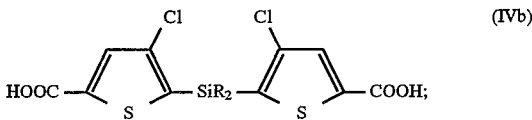 (IVb)

and (2) removing the silyl group SiR₂ from the product of step (1).

* * * * *